United States Patent
Nabeta

(10) Patent No.: US 8,168,670 B2
(45) Date of Patent: May 1, 2012

(54) PYRAZOLONE DERIVATIVE EMULSION FORMULATIONS

(75) Inventor: Kiichiro Nabeta, Tokyo (JP)

(73) Assignees: Teikoku Pharma USA, Inc., San Jose, CA (US); Techno Guard Co., Ltd., Kawasaki, Kanagawa (JP)

( * ) Notice: Subject to any disclaimer, the term of this patent is extended or adjusted under 35 U.S.C. 154(b) by 601 days.

(21) Appl. No.: 12/267,304

(22) Filed: Nov. 7, 2008

(65) Prior Publication Data

US 2009/0131496 A1    May 21, 2009

Related U.S. Application Data

(60) Provisional application No. 60/989,707, filed on Nov. 21, 2007.

(51) Int. Cl.
*A61K 31/415* (2006.01)
*C07D 231/10* (2006.01)
*C07D 231/52* (2006.01)

(52) U.S. Cl. .................. 514/404; 548/371.1; 548/368.7

(58) Field of Classification Search .......................... None
See application file for complete search history.

(56) References Cited

U.S. PATENT DOCUMENTS

| | | | | |
|---|---|---|---|---|
| 4,211,836 A | * | 7/1980 | Yoneyama et al. | 430/449 |
| 4,360,518 A | * | 11/1982 | Rovee et al. | 514/174 |
| 7,211,596 B2 | * | 5/2007 | Yoshida et | 514/404 |
| 2003/0162775 A1 | * | 8/2003 | Singh et al. | 514/227.8 |
| 2005/0276763 A1 | | 12/2005 | Pfeifer et al. | |
| 2006/0189682 A1 | | 8/2006 | Payne et al. | |
| 2007/0116729 A1 | | 5/2007 | Palepu | |

OTHER PUBLICATIONS

Higashi et al, Edaravone (3-methyl-1-phenyl-2-pyrazolin-5-one), a novel free radical scavenger, for treatment of cardiovascular diseases. Rec. Pat. Cardio. Drug Disc. 2006;1:85-93.

* cited by examiner

*Primary Examiner* — Sreeni Padmanabhan
*Assistant Examiner* — Svetlana M Ivanova
(74) *Attorney, Agent, or Firm* — Brett E. Field; Brian E. Davy; Bozicevic, Field & Francis, LLP

(57) ABSTRACT

Pyrazolone derivative emulsion formulations are provided. The emulsion formulations include a pyrazolone derivative active agent, e.g., Edaravone, oil, water and an emulsifier. Also provided are methods of making and using the subject emulsion formulations.

22 Claims, No Drawings

PYRAZOLONE DERIVATIVE EMULSION FORMULATIONS

CROSS-REFERENCE TO RELATED APPLICATIONS

Pursuant to 35 U.S.C. § 119 (e), this application claims priority to the filing date of U.S. Provisional Patent Application Ser. No. 60/989,707 filed Nov. 21, 2007; the disclosure of which is herein incorporated by reference.

INTRODUCTION

3-Methyl-1-phenyl-2-pyrazolin-5-one (which is also known as Edaravone) is a compound having use in a variety of different treatment applications. Some applications in which Edaravone has found use is in the treatment of cerebrovascular disorders such as cerebral stroke, brain tumor, cerebral ischemia observed in the acute stage of head trauma, cerebral edema and the like.

Injection formulations containing Edaravone as an active ingredient have been developed. One example of an injection formulation of Edaravone is an aqueous solution of Edaravone containing at least one compound selected from sulfites, hydrogensulfites and pyrosulfites, and a cysteine and has a pH in the range of 2.5 to 6.0 (Japanese patent publication (Kokoku) No. Hei 7-121861).

Injection formulations of Edaravone are challenging to prepare. Edaravone is sparingly soluble in water (2 mg/mL at 25° C.). Furthermore, Edaravone exhibits less chemical stability with an increase in its concentration in an aqueous solution. In addition, Edaravone is prone to decompose by oxidation in an aqueous solution. In consideration of such properties, it is difficult to stabilize Edaravone as a pharmaceutical for a long period time and prepare an injection containing Edaravone in an amount exceeding a saturated solubility in water.

There is a need for the development of an injection formulation that contains a high-concentration of Edaravone, where the formulation is storage-stable.

SUMMARY

Pyrazolone derivative emulsion formulations are provided. The emulsion formulations include a pyrazolone derivative, e.g., Edaravone, oil, water and an emulsifier. Also provided are methods of making and using the subject emulsion formulations.

DEFINITIONS

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Alkyl" refers to monovalent saturated aliphatic hydrocarbyl groups having up to 10 carbon atoms, or up to 9 carbon atoms, up to 8 carbon atoms, or up to 3 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Cycloalkyl" refers to cyclic hydrocarbyl groups having from 3 to 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of such heterocyclic non-aromatic rings include, but are not limited to, aziridinyl, azetidinyl, piperazinyl, and piperidinyl.

"Heteroaryl" refers to a stable heterocyclic aromatic ring and fused rings containing one or more heteroatoms independently selected from N, O and S. A fused heterocyclic ring system may include carbocyclic rings and need only include one heterocyclic ring. Examples of such heterocyclic aromatic rings include, but are not limited to, pyridine, pyrimidine, and pyrazinyl.

"Aryl" refers to a monovalent aromatic hydrocarbon group derived by the removal of one hydrogen atom from a single carbon atom of a parent aromatic ring system. Typical aryl groups include, but are not limited to, groups derived from benzene, ethylbenzene, mesitylene, toluene, xylene, aniline, chlorobenzene, nitrobenzene, and the like.

"Aralkyl" or "arylalkyl" refers to an alkyl group, as defined above, substituted with one or more aryl groups, as defined above.

"Halogen" refers to fluoro, chloro, bromo and iodo. In some embodiments, the halogen is fluoro or chloro.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryl, substituted thioaryl, thioketo, thiol, alkyl-S(O)—, aryl-S(O)—, alkyl-S(O)2- and aryl-S(O)2-.

DETAILED DESCRIPTION

Pyrazolone derivative emulsion formulations are provided. The emulsion formulations include a pyrazolone derivative, e.g., Edaravone, oil, water and an emulsifier. Also provided are methods of making and using the subject emulsion formulations.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, the subject emulsion formulations are described first in greater detail, followed by a review of methods for preparing the formulations, and a discussion of various illustrative applications in which the subject formulations find use.

Emulsion Formulations

Aspects of the invention include emulsion formulations of a pyrazolone derivative. As the formulations are emulsions, the formulations are liquid preparations that are a suspension of small globules of one liquid in a second liquid with which the first liquid will not mix. Emulsions in accordance with the present invention include a pyrazolone derivative active agent, oil, water and an emulsifier.

Aspects of the invention include storage-stable emulsion formulations. By storage-stable is meant that the compositions may be stored for extended periods of time without significant phase separation and/or significant reduction in activity of the pyrazolone active agent. In certain embodiments, the subject compositions are stable for 2 months or longer, such as 4 months or longer, including 6 months or longer, e.g., at 1 year or longer, 1.5 years or longer, etc., when maintained at 25° C. By the phrase "without substantially decreasing the activity of the pyrazolone derivative active agent" is meant that at the end of the storage period, there is less than about 10% reduction in activity of the pyrazolone derivative active agent compared to the beginning of the storage period. In certain embodiments, the formulations exhibit substantially no (if any) color change over an extended period of time when maintained at 25° C., where by "extended period of time" is meant 2 months or longer, such as 4 months or longer, including 6 months or longer, e.g., at 1 year or longer, 1.5 years or longer, etc.

In certain embodiments, the emulsion formulations of the invention are alcohol free. As such, the formulations do not include an amount of an alcohol, e.g., ethanol. In certain embodiments, the formulations are reductant free, e.g., they are sulfite free. In certain embodiments, the formulations are free of a stabilizer, such as a chelating agent, e.g., ethylenediamine, calcium disodium edetate or disodium edetate.

As summarized above, formulations of the invention include a pyrazolone derivative active agent, which active agent may be a pyrazolone derivate, e.g., as specified below, or a physiologically acceptable salt thereof, or hydrate thereof. Of interest are pyrazolone derivatives of the following formula (I)

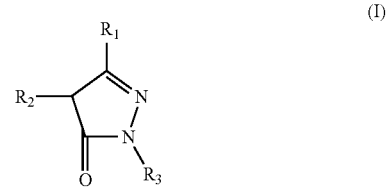

wherein:

$R_1$ represents hydrogen atom, an aryl, an alkyl having 1 to 5 carbon atoms or an alkoxycarbonylalkyl having 3 to 6 carbon atoms in total; $R_2$ represents hydrogen atom, an aryloxy, an arylmercapto, an alkyl having 1 to 5 carbon atoms or a hydroxyalkyl having 1 to 3 carbon atoms; or $R_1$ and $R_2$ are coupled together to form an alkylene having 3 to 5 carbon atoms; and $R_3$ is hydrogen atom, an alkyl having 1 to 5 carbon atoms, a cycloalkyl having 5 to 7 carbon atoms, a hydroxyalkyl having 1 to 3 carbon atoms, benzyl, a naphthyl or phenyl, or a phenyl substituted by 1 to 3 substituents, which may be the same or different and selected from the group consisting of an alkoxy having 1 to 5 carbon atoms, a hydroxyalkyl having 1 to 3 carbon atoms, an alkoxycarbonyl having 2 to 5 carbon atoms in total, an alkylmercapto having 1 to 3 carbon atoms, an alkylamino having 1 to 4 carbon atoms, a dialkylamino having 2 to 8 carbon atoms in total, a halogen atom, trifluoromethyl, carboxyl, cyano, hydroxyl group, nitro, amino and acetamido) or physiologically acceptable salt thereof, or a hydrate or solvate thereof. 2.

In certain embodiments, the pyrazolone derivative is 3-Methyl-1-phenyl-2-pyrazolin-5-one (non-proprietary name: "Edaravone", trade name: "Radicut"; manufactured and sold by Mitsubishi Pharma Corporation, hereinafter referred to as Edaravone) which is also called 3-methyl-1-phenyl-5-pyrazolone. This particular pyrazolone derivative has the structure (II):

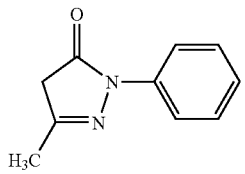

The pyrazolone active agent may be present as the pyrazolone compound, a physiologically acceptable salt thereof, or a hydrate thereof.

Embodiments of the subject formulations are characterized by having high concentrations of active agent. In certain embodiments, the pyrazolone active agent in the composition is 1.0 mg/ml or higher, including 1.5 mg/ml or higher, and in certain embodiments ranges from 1.0 to 30 mg/ml, such as 1.5 to 15 mg/ml, including 1.5 to 6.0 mg/ml.

Emulsions formulations of the invention are emulsions of water and oil. As the formulations are emulsions, they are mixtures of two immiscible (unblendable) fluids, where one fluid (an oil or water) (the dispersed phase) is dispersed in the other fluid (an oil or water) (the continuous phase). The combination ratio of the oil and the emulsifier in the present invention is not particularly limited as long as a lipid emulsion can be obtained.

As the subject compositions include an emulsion of oil and water, they include water that may be present in an amount that ranges, in certain embodiments, from about 70% to about 99%, such as from about 80% to about 95%. The water may be any convenient water, include deionized water, water for injection (WFI), etc.

Also present in the subject emulsion formulations is an oil phase. Oils of interest are physiologically acceptable and include, but are not limited to: simple lipids, derived lipids, and complex lipids that are derived from natural vegetable oil and fat, animal oil and fat, and mineral oil, or a mixture of those. In certain embodiments, the oil is chosen from soybean oil, olive oil, sesame oil, castor oil, corn oil, peanut oil, safflower oil, rape seed oil, eucalyptus oil, medium-chain fatty acid ester, and low-chain fatty acid ester. Animal oils and fat of interest include, but are not limited to, cod-liver oil, seal oil, sardine oil, docosahexaenoic acid, and eicosapentaenoic acid. Mineral oils of interest include, but are not limited to, liquid paraffins. One or a combination of more than one of these can be used. Soybean oil, olive oil, and sesame oil are employed in certain embodiments. Highly refined oils and fats are employed in certain embodiments. Soybean oil and olive oil are employed in certain embodiments. In general, the amount of oil in the formulation composition should be 0.1 to 100 mg/ml, such as 0.1 to 10 mg/ml and including 0.1 to 3 mg/ml.

Also present in the subject emulsion formulations is an emulsifying agent. Emulsifying agents to be used for the present invention include any type of emulsifier that has been used for pharmaceutical formulations, including, phospholipid, nonionic surfactant, or a mixture of such agents. Refined phospholipids. such as egg-yolk lecithin and soybean lecithin are employed in certain embodiments. Refined phospholipid may include phosphatidylinocytol, phosphatidyl ethanolamine, phosphatidylserine, and sphingomyeline with phosphatidylcholine as a main ingredient. Nonionic surfactant of interest include, but are not limited to, polyethylene glycol, polyoxyalkylene copolymer, and sorbitan fatty acid ester. One or a combination of more than one of these emulsifiers can be used. In certain embodiments, a refined emulsifier is employed. A refined phospholipid derived from egg-yolk or soybean oil with phosphatidylcholine as a main ingredient is employed in certain embodiments. The amount of emulsifier may vary, ranging in certain embodiments from 0.01 to 30 mg/ml, such as 0.1 to 20 mg/ml.

Certain embodiments of the formulations also include one or more emulsification enhancers. Any type of fatty acid that has been used for pharmaceutical formulations can be used as an emulsification enhancer. Of interest are fatty acids with the carbon number of from 6 to 22, either natural or synthetic, and either saturated fatty acid or unsaturated fatty acid can be used, including but not limited to stearic acid, oleic acid, linoleic acid, palmitic acid, linolenic acid, and myristic acid. Refined fatty acids, e.g., oleic acid, are employed in certain embodiments. In certain embodiments, the amount of emulsification enhancer ranges from 0.002 to 3 mg/ml, such as from 0.02 to 3 mg/ml.

In certain embodiments, a pH adjusting agent is also present. pH adjusting agents of interest include, but are not limited to: sodium hydrochloride, hydrochloric acid, phosphoric acid buffer solution, and citric acid buffer solution. The pH of the emulsion of the present invention can be adjusted at 5.5 to 7.5 by using the pH adjusting agent.

Other additives that may be present in the formulation, as desired (e.g., stabilizing agents), include but are not limited to: glycerin, propylene glycol, polyethylene glycol (especially the average molecular weight of 400), maltose, mannitol, sorbitol, xylitol, sucrose, trehalose and inositol.

Preparation Methods

The emulsion formulations of the invention can be prepared using any convenient protocol. In one embodiment, an injection solvent, e.g., WFI, is added to a smooth mixture of a suitable oil. After the mixture is roughly emulsified, it is then finely emulsified, e.g., by using a high pressure emulsification machine. For rough emulsification, Homomixer (Mizuho Industrial Co., Ltd.) or High Flex Disperser (SMT) can be used. For fine emulsification, a high pressure homogenizer such as Gaulin Homogenizer (APV-SMT) and Microfluidizer (Microfluidics) can be used. In case of using a high pressure homogenizer, the emulsion may be run through 2 to 50 times, such as 5 to 20 times, with a pressure of approximately 500 to 1000 kg/cm$^2$. The procedure of mixing and emulsifying can be carried out at a room temperature or at the temperature lower than the room temperature. In certain embodiments, the above preparation is made with nitrogen gas.

Methods of Use

The subject emulsion formulations find use in parenteral administration, e.g., via injection of, a pyrazolone derivative, e.g., Edaravone, to a subject. By "parenteral administration" is meant delivery by a protocol that delivers a quantity of the subject emulsion formulations to a patient by a route other than the digestive tract, e.g., via a pulmonary route, via intramuscular injection, via intravenous delivery, etc. In certain embodiments, parenteral administration is by injection using an injection delivery device.

In certain embodiments, methods of the invention include a diagnostic step. Individuals may be diagnosed as being in need of the subject methods using any convenient protocol, and are generally known to be in need of the subject methods, e.g., they are suffering from a target disease condition or have been determined to be at risk for suffering from a target disease condition, prior to practicing the subject methods.

Utility

The subject formulations methods find use in a variety of applications. The subject formulations and methods find use in any application where a subject would benefit from being administered a pyrazolone derivative active agent, such as Edaravone. In certain embodiments, the subject methods and formulations are employed in treating conditions where antioxidant activity is desired, e.g., via enhanced prostacyclin production, inhibition of lypoxygenase metabolism of arachidonic acid, inhibition of alloxan-induced lipid peroxidation, and quenching of active oxygen. General types of applications of interest include, but are not limited to the treatment of myocardial and vascular injury following ischemia and reperfusion in patients with acute myocardial infarction, atherosclerosis and chronic phase. Specific applications of interest include the treatment of cerebrovascular disorders (e.g., cerebral stroke, brain tumor, cerebral ischemia observed in the acute stage of head trauma, cerebral edema, etc.); amyotrophic lateral sclerosis, mitochondrial myopathy, etc.

By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g., terminated, such that the host no longer suffers from the condition, or at least the symptoms that characterize the condition.

Particular applications in which the subject methods and compositions find use include those described in U.S. Pat. No. 7,211,596; the disclosure of which is herein incorporated by reference in its entirety. See also Higashi et al., "Edaravone (3-Methyl-1-Phenyl-2-Pyrazolin-5-one), A Novel Free Radical Scavenger, for Treatment of Cardiovascular Diseases," Recent patents on Cardiovascular Drug Discovery (2006) 1:85-93, the disclosure of which is herein incorporated by reference in its entirety.

Kits

Also provided are kits that find use in practicing the subject methods, as described above. For example, kits for practicing the subject methods may a quantity of the emulsion composition, present in unit dosages, e.g., ampoules, or a multi-dosage format. As such, in certain embodiments the kits may one or more unit dosages (e.g., ampoules) of the emulsion formulation. In yet other embodiments, the kits may include a single multi dosage amount of the emulsion formulation.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

A. Formulation Preparation

Preparation Example 1

200 mg of refined soybean oil, 3.6 g of refined egg-yolk lecithin, and 480 mg of oleic acid were stirred together with nitrogen gas at 40° C. 300 mg of Edaravone was added to the mixture and stirred altogether with nitrogen gas at 40° C. 4.42 g mg of propylene glycol, 20 g of mannitol and 150 ml of distilled water for injection that was combined in advance was added to the mixture and it was roughly emulsified with High Flex Disperser (11,300 rpm×15 min) with nitrogen gas at 40° C. The distilled water was added to the emulsion to make it 200 ml. After a proper amount of sodium hydroxide was added to this lipid emulsion and the pH was adjusted to fall within the neutral range of 6.0 to 6.5, it was further emulsified with a high pressure homogenizer (800 kg/cm$^2$). The emulsion was filtered through a membrane filter (pore size 0.45 µm). The filtered lipid emulsion was poured in a 5 ml ampoule and the ampoule was sealed with nitrogen added to it. The ampoule was sterilized under the condition of 121° C. for 10 minutes to be used as a sample.

Preparation Example 2

200 mg of refined soybean oil, 3.6 g of refined egg-yolk lecithin, and 480 mg of oleic acid were stirred together with nitrogen gas at 40° C. 600 mg of Edaravone was added to the mixture and stirred altogether with nitrogen gas at 40° C. 4.42 g of propylene glycol, 20 g of mannitol and 150 ml of distilled water for injection that was combined in advance was added to the mixture and it was roughly emulsified with High Flex Disperser (11,300 rpm×15 min) with nitrogen gas at 40° C. The distilled water was added to the emulsion to make it 200 ml. After a proper amount of sodium hydroxide was added to this lipid emulsion and the pH was adjusted to fall within the neutral range of 6.0 to 6.5, it was further emulsified with a high pressure homogenizer (800 kg/cm$^2$). The emulsion was filtered through a membrane filter (pore size 0.45 µm). The filtered lipid emulsion was poured in a 5 ml ampoule and the ampoule was sealed with nitrogen added to it. The ampoule was sterilized under the condition of 121° C. for 10 minutes to be used as a sample.

Preparation Example 3

200 mg of refined soybean oil, 3.6 g of refined egg-yolk lecithin, and 480 mg of oleic acid were stirred together with nitrogen gas at 40° C. 300 mg of Edaravone was added to the mixture and stirred altogether with nitrogen gas at 40° C. 4.42 g of propylene glycol, 20 g of sorbitol and 150 ml of distilled water for injection that was combined in advance was added to the mixture and it was roughly emulsified with High Flex Disperser (11,300 rpm×15 min) with nitrogen gas at 40° C. The distilled water was added to the emulsion to make it 200 ml. After a proper amount of sodium hydroxide was added to this lipid emulsion and the pH was adjusted to fall within the neutral range of 6.0 to 6.5, it was further emulsified with a high pressure homogenizer (800 kg/cm$^2$). The emulsion was filtered through a membrane filter (pore size 0.45 µm). The filtered lipid emulsion was poured in a 5 ml ampoule and the ampoule was sealed with nitrogen added to it. The ampoule was sterilized under the condition of 121° C. for 10 minutes to be used as a sample.

Preparation Example 4

200 mg of refined soybean oil, 3.6 g of refined egg-yolk lecithin, and 480 mg of oleic acid were stirred together with nitrogen gas at 40° C. 600 mg of Edaravone was added to the mixture and stirred altogether with nitrogen gas at 40° C. 4.42 g of propylene glycol, 20 g of sorbitol and 150 ml of distilled water for injection that was combined in advance was added to the mixture and it was roughly emulsified with High Flex Disperser (11,300 rpm×15 min) with nitrogen gas at 40° C. The distilled water was added to the emulsion to make it 200 ml. After a proper amount of sodium hydroxide was added to this lipid emulsion and the pH was adjusted to fall within the neutral range of 6.0 to 6.5, it was further emulsified with a high pressure homogenizer (800 kg/cm$^2$). The emulsion was filtered through a membrane filter (pore size 0.45 µm). The filtered lipid emulsion was poured in a 5 ml ampoule and the ampoule was sealed with nitrogen added to it. The ampoule was sterilized under the condition of 121° C. for 10 minutes to be used as a sample.

B. Formulation Evaluation

1. Content Measurement

The content of Edaravone in the sample prepare in Preparative Examples 1-4, as well as the commercially available Edaravone formulation sold under the name of Radicut by Mitsubhishi Pharma Corporation (Japan) was measured by HPLC with the following conditions.
Column: Nova-Pak 4 µm, C18 (3.9×150 mm)
Mobile Phase: H$_2$O: MeOH=6:4
Flow Speed: 0.5 ml/min.
Detector: UV Detector (244 nm)
Column Temperature: 35° C.

C. Comparative Results of Preparative Examples 1-4

The stability of the compounds prepared by Preparative Examples 1-4 were tested and compared to Radicut (Mitsubishi Pharma Corporation). Table 1 shows the amount of Edaravone in samples from Preparative Examples and Radicut over the cited time periods.

TABLE 1

| Stability test; accelerated test (40° C.) Edaravone Content | | | | | |
|---|---|---|---|---|---|
| | Preparative Example 1 | Preparative Example 2 | Preparative Example 3 | Preparative Example 4 | Radicut |
| 0 Month | 100.0% | 100.0% | 100.0% | 100.0% | 100.0% |
| 1 Month | 99.1% | 101.5% | 100.8% | 101.9% | 100.0% |
| 3 Month | 97.8% | 99.5% | 96.2% | 100.3% | 100.7% |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An emulsion formulation comprising:
   a pyrazolone derivative active agent;
   oil;
   water ranging from about 80% to about 95%; and
   an emulsifier chosen from egg-yolk phospholipid or soybean phospholipid, wherein said emulsion formulation is formulated for injection into a subject.

2. The emulsion formulation according to claim 1, wherein said emulsion formulation has a pH ranging from 5.5 to 7.5.

3. The emulsion formulation according to claim 1, wherein said formulation is alcohol free.

4. The emulsion formulation according to claim 1, wherein said formulation is reductant free.

5. The emulsion formulation according to claim 1, wherein said formulation is chelator free.

6. The emulsion formulation according to claim 1, wherein said pyrazolone derivative active agent is present in an amount ranging from 1.0 to 30 mg/ml.

7. The emulsion formulation according to claim 1, wherein said oil is present in an amount ranging from 0.1 to 10 mg/ml.

8. The emulsion formulation according to claim 1, wherein said emulsion further comprises an emulsification enhancer.

9. The emulsion formulation according to claim 1, wherein said pyrazolone derivative active agent is Edaravone or a physiologically acceptable salt thereof or hydrate thereof.

10. A kit comprising an emulsion formulation comprising:
    a pyrazolone derivative active agent; oil;
    water ranging from about 80% to about 95%; and
    an emulsifier chosen from egg-yolk phospholipid or soybean phospholipid, wherein said emulsion formulation is formulated for injection into a subject.

11. The kit according to claim 10, wherein said emulsion formulation has a pH ranging from 5.5 to 7.5.

12. The kit according to claim 10, wherein said formulation is alcohol free.

13. The kit according to claim 10, wherein said formulation is reductant free.

14. The kit according to claim 10, wherein said formulation is chelator free.

15. The kit according to claim 10, wherein said pyrazolone derivative active agent is present in an amount ranging from 1.0 to 30 mg/ml.

16. The kit according to claim 10, wherein said oil is present in an amount ranging from 0.1 to 10 mg/ml.

17. The kit according to claim 10, wherein said emulsion further comprises an emulsification enhancer.

18. The kit according to claim 10, wherein said pyrazolone derivative active agent is Edaravone or a physiologically acceptable salt thereof or hydrate thereof.

19. The emulsion formulation of claim 1, wherein said emulsion formulation is storage-stable.

20. The emulsion formulation of claim 10, wherein said emulsion formulation is storage-stable.

21. An emulsion formulation comprising:
a pyrazolone derivative active agent;
oil present in an amount ranging from 0.1 to 10 mg/ml;
water ranging from about 80% to about 95%;
an emulsifier chosen from egg-yolk phospholipid or soybean phospholipid; and
an emulsification enhancer,
wherein said emulsion formulation is formulated for injection into a subject.

22. The emulsion formulation according to claim 21, wherein said pyrazolone derivative active agent is Edaravone or a physiologically acceptable salt thereof or hydrate thereof.

* * * * *